United States Patent [19]

Rose et al.

[11] 4,433,172
[45] Feb. 21, 1984

[54] PRODUCTION OF DIHYDROXY ARYLOPHENONES

[75] Inventors: John B. Rose, Letchworth; Michael B. Cinderey, Knebworth, both of England

[73] Assignee: Imperial Chemical Industries PLC, London, England

[21] Appl. No.: 410,995

[22] Filed: Aug. 24, 1982

[30] Foreign Application Priority Data

Sep. 17, 1981 [GB] United Kingdom ............... 8128177

[51] Int. Cl.$^3$ ............................................. C07C 45/54
[52] U.S. Cl. .................................................. 568/319
[58] Field of Search ............... 568/333, 309, 319, 322

[56] References Cited

U.S. PATENT DOCUMENTS

| 2,675,411 | 4/1954 | Caldwell | 568/333 |
| 2,818,436 | 12/1957 | Prill | 568/309 |
| 2,876,210 | 3/1959 | Wynn et al. | 568/333 |
| 2,879,297 | 3/1959 | Prill et al. | 568/309 |

FOREIGN PATENT DOCUMENTS

| 1139111 | 11/1962 | Fed. Rep. of Germany | 568/309 |
| 542805 | 11/1973 | Switzerland | 568/309 |
| 1378913 | 12/1974 | United Kingdom | 568/309 |
| 1415011 | 11/1975 | United Kingdom | 568/309 |

OTHER PUBLICATIONS

Hacking, J. Chem. Tech. Biotechnol., vol. 30, pp. 626–641, (1980).
Effenberger et al., Angew. Chemie Int. Ed., vol. 12, pp. 775–776, (1973).

Primary Examiner—James H. Reamer
Attorney, Agent, or Firm—Cushman, Darby & Cushman

[57] ABSTRACT

Production of a dihydroxy arylophenone by reacting a diaryl carbonate in the presence of a fluoroalkane sulphonic acid. The diaryl carbonate is preferably diphenyl carbonate, the product so formed being 4,4'-dihydroxy-benzophenone. The sulphonic acid is preferably trifluoromethane sulphonic acid.

3 Claims, No Drawings

PRODUCTION OF DIHYDROXY ARYLOPHENONES

The present invention relates to a process for the production of dihydroxy arylophenones.

Hydroxy arylophenones are commercially useful substances and have been employed, for example, in the preparation of dyestuffs, polymers and ultraviolet light absorption agents.

Conventional prior art processes for making hydroxy arylophenones include aromatic acylation using an aromatic acid chloride and a Friedels-Craft catalyst such as $AlCl_3$, or an aromatic ester Fries rearrangement, also using a metallic halide catalyst such as $AlCl_3$, the ester having been formed from a phenol and an aromatic acid chloride. It is also known to prepare hydroxy arylophenones by aromatic acylation using an aromatic carboxylic acid, with liquid HF being employed as a condensing agent.

We have now discovered a new and extremely convenient process for preparing dihydroxy arylophenones in high yield which does not require the use of liquid HF (the use of which is to be avoided if possible because of its extremely corrosive properties and physiologically harmful action and the need to employ pressure equipment) or the use of a metallic halide catalyst (which can leave harmful residues).

According to the present invention there is provided a process for the production of a dihydroxy arylophenone which comprises reacting a diaryl carbonate of formula H—Ar'—O—CO—O—Ar—H, where Ar and Ar' which may be the same or different are each an aryl radical comprising a benzenoid ring which is bonded to the carbonate group and has a nuclear hydrogen atom H— positioned para to the carbonate linkage, with a fluoroalkane sulphonic acid to produce a dihydroxy arylophenone of formula HO—Ar'—CO—Ar—OH.

It has thus been discovered that diaryl carbonates (as defined) will rearrange in fluoroalkane sulphonic acids to yield dihydroxy arylophenones in high yield.

Examples of fluoroalkane sulphonic acids which may be used particularly include trifluoromethane sulphonic acid and difluoromethane sulphonic acid.

The aromatic radicals Ar' and Ar may be nuclear unsubstituted (apart from the carbonate substituent), particularly in the benzenoid ring, or have one or more nuclear substituents provided that the substituent(s) does not deleteriously affect the rearrangement to the dihydroxy arylophenone.

A preferred diaryl carbonate for use according to the invention is diphenyl carbonate. Under the condition of the process of the invention, this rearranges to 4,4'-dihydroxy-benzophenone.

The amount of fluoroalkane sulphonic acid to use should preferably be such that there are at least 3, and more preferably 5, moles of fluoroalkane sulphonic acid per mole of diaryl carbonate (eg 5-20 moles fluoroalkane sulphonic acid per mole of diaryl carbonate); the fluoroalkane sulphonic acid, if liquid, then acts as an effective solvent and catalyst for the reaction.

The present invention is illustrated by the following Example.

EXAMPLE

The following were charged to a 100 ml three-necked flask provided with an addition funnel, nitrogen flow, air condenser and stirrer; diphenyl carbonate (20 g; 0.093 mole) followed by trifluoromethane sulphonic acid (75 ml). A straw-coloured solution was obtained. The stirred reaction mixture was heated at 120° C. for 3 hours and then at 105° C. for 17 hours. The stirred reaction mixture was then added dropwise to 800 ml demineralised water. The solid of the resulting slurry was separated by filtration, washed twice with water, reslurried in 400 ml of water, separated again by filtration, washed twice with water, and dried at 100° C. for 1 hour and then at 80° C. over the week-end. The yield of material obtained was 11.33 g (56%). The infra-red spectrum of the product was identical with that of an authentic specimen of 4,4'-dihydroxy-benzophenone; its melting point (after recrystallisation) was 219.5°–221° C.

We claim:

1. A process for the production of 4,4'-dihydroxybenzophenone which comprises reacting diphenyl carbonate in the presence of a fluoroalkane sulphonic acid.

2. A process according to claim 1 wherein the fluoroalkane sulphonic acid employed is trifluoromethane sulphonic acid.

3. A process according to claim 1 wherein the fluoroalkane sulphonic acid employed is difluoromethane sulphonic acid.

* * * * *